United States Patent

Pozzi

[11] Patent Number: 5,261,815
[45] Date of Patent: * Nov. 16, 1993

[54] DENTAL TOOTH SHADE/HUE MATCHING REFERENCE SYSTEM

[75] Inventor: Bruno Pozzi, Camarillo, Calif.

[73] Assignee: American Tooth Industries, Oxnard, Calif.

[*] Notice: The portion of the term of this patent subsequent to Nov. 19, 2008 has been disclaimed.

[21] Appl. No.: 872,608

[22] Filed: Apr. 23, 1992

Related U.S. Application Data

[63] Continuation-in-part of Ser. No. 686,809, Apr. 17, 1991, Pat. No. 5,066,227, and a continuation-in-part of Ser. No. 791,155, Nov. 13, 1991.

[51] Int. Cl.$^5$ .................................................. A61C 19/10
[52] U.S. Cl. .................................................. 433/26
[58] Field of Search .................................................. 433/26

[56] References Cited

U.S. PATENT DOCUMENTS

| | | | |
|---|---|---|---|
| 2,341,153 | 2/1944 | Myerson | 433/26 |
| 3,436,156 | 4/1969 | Adler et al. | 433/26 |
| 4,115,922 | 9/1978 | Alderman | 433/26 |
| 4,747,776 | 5/1988 | Sudderth | 433/26 |
| 4,802,850 | 2/1989 | Boon | 433/26 |

FOREIGN PATENT DOCUMENTS

| 2464699 | 4/1981 | France | 433/26 |
|---|---|---|---|

*Primary Examiner*—John J. Wilson
*Attorney, Agent, or Firm*—Emrich & Dithmar

[57] ABSTRACT

A system for providing artificial teeth with lifelike shade and hue, or for matching the shade and hue of an artificial tooth with the shade and hue of one's natural teeth, employs a single-sided master shade/hue guide and a plurality of paired sample teeth, with each pair attached to a holder and having the same shade and hue corresponding to a tooth on the master shade/hue guide. The artificial sample teeth on the single-sided master shade/hue guide are arranged either by shade from light to dark or by hue, with the teeth grouped by color and sequenced from light to dark within. The master shade/hue guide as well as each pair of shade/hue matched sample teeth includes a respective background panel disposed aft of and extending above the aligned sample teeth for providing a uniform background color field for optimum viewing of the sample teeth. The master shade/hue guide as well as each pair of shade/hue matched sample teeth is also adapted for use with a background tab positioned aft of the sample teeth and adapted for insertion in a patient's mouth which allows for choosing the correct shade/hue by juxtaposed comparison of sample teeth with the patient's natural teeth. The background tab provides an extended uniform color field background for highly accurate comparison and selection of artificial teeth shade and hue. In addition, the background tab is inexpensive and disposable eliminating the requirement to sterilize the shade/hue guide or matched pairs of sample teeth prior to use by another patient.

23 Claims, 3 Drawing Sheets

DENTAL TOOTH SHADE/HUE MATCHING REFERENCE SYSTEM

CROSS-REFERENCE TO RELATED APPLICATION

This is a continuation-in-part of applications Ser. Nos. 686,809, now U.S. Pat. No. 5,066,227 and 791,155, pending respectively filed Apr. 17, 1991 and Nov. 13, 1991, in the name of the present inventor for IMPROVED DENTAL TOOTH SHADE/HUE MATCHING REFERENCE SYSTEM.

FIELD OF THE INVENTION

This invention relates generally to the fabrication of denture appliances and is particularly directed to an improved system for providing artificial teeth with a life-like color and shade.

BACKGROUND OF THE INVENTION

Dental appliances such as false teeth and bridges have become more commonplace as the number of senior citizens increases, as such appliances become more affordable, and as concern with personal appearance increases. The fabrication of dental appliances by either a dentist or technician has been simplified with the advent of plastic teeth, while bridge supports have facilitated the accurate reconstruction of teeth configurations. While the structural integrity and useful lifetime of such dental appliances are of the utmost importance, the appearance and aesthetics of such structures are also of considerable importance to most users and potential users. Increasingly the cost and time involved in reconstructing a patient's teeth are devoted to aesthetics considerations such as the color, shade and other characteristics of the artificial teeth in the dental appliance. The goal is, of course, to match the newly installed artificial teeth in shade and hue as closely as possible with the patient's remaining teeth and to provide a most natural appearance for the user. It is also desirable, once the proper hue is determined to provide a progressively darker shade in the same hue, where multiple teeth are needed and the replacement teeth are to be located toward the rear of the mouth.

The dentist's first task is to prepare the patient's mouth in order to fabricate the dental appliance, commonly referred to as "dentures" such as a partial, a crown, a bridge, veneers, laminates, or over dentures. With the patient's mouth prepared, an impression of the patient's mouth is then obtained. The dentist must then determine the shade and color, or hue, of any artificial teeth in the dental appliance.

Shade matching or shade progression is generally accomplished by means of a shade guide 18 such as shown in FIG. 1. A typical prior art shade guide 18 includes an elongated, linear holder 10 containing a plurality of specimens 12. Each of the specimens is comprised of a sample tooth 14 and a support member 16 for attaching the sample tooth to the holder 10. Each sample tooth 14 is provided with a predetermined shade and hue for matching with the patient's natural teeth. Shade guides are typically provided by manufacturers of prefabricated teeth for use as dentures, partials and implants over dentures. Crowns, bridges, laminates and veneers are, on the other hand, generally manufactured by dental laboratories using tooth powder materials (resins or porcelain) which have also been fabricated by tooth manufacturers.

The conventional prior art shade guide 18 such as shown in FIG. 1 includes an average of twelve shade selections fixedly mounted in sequence on the common holder 10. The dentist must match one of these shades to the shade of existing teeth in the patient's mouth. If the patient is edentulous, the dentist, together with the patient, typically selects a hue and shade progression according to the age of the patient based upon the dentist's experience with the patient's approval. Once a hue and shade progression are selected, the doctor records the shade numbers and/or brand of teeth or material on a prescription. The prescription together with the patient's impression, which is usually comprised of hydrocolloid, silicone, alginate or rubber base, are sent to a laboratory for fabrication of a dental appliance. The laboratory set-up man or master technician selects the teeth for dentures, partials or implant over dentures, or the tooth materials for crowns, bridges, laminates or veneers by matching the shade number provided by the dentist in the prescription.

Although in widespread use, this approach is not error-proof, nor does it guarantee a perfect match for several reasons. For example, the shade guide used by the dentist is not the same as that used by the laboratory. The shade and hue of the materials used in a shade guide change with time, e.g., color intensity is reduced and colors tend to lighten, or fade, over time. This is particularly true where the shade guide is overexposed to sunlight or frequently disinfected, or sterilized, resulting in a change in the original tones. In addition, the doctor or fabricating technician may misread the color number on the shade guide or the shade guide manufacturer may erroneously identify the shade of one or more specimens in the shade guide. Finally, the tooth manufacturer may slightly change the shades of teeth or tooth powder in its production batches because of changes, which frequently depend on availability, of one or more ingredients. The occurrence of any of these events will result in an inaccurate matching of artificial teeth shade with the shade of natural teeth because the technician normally does not have access to the patient and was not present at the initial shade selection by the dentist.

While most mechanical problems with dental appliances can be corrected at chair side, the problems of shade matching discussed above cannot generally be thus corrected and typically require a return of the dental appliance to the denture manufacturer or lab resulting in patient inconvenience and dentist loss of labor time.

The present invention addresses the aforementioned problems of the prior art by providing an improved dental tooth shade matching reference system which provides the dentist as well as the tooth fabricating technician with a specimen precisely matched in shade and hue with the patient's natural teeth. Patient identifying labels are provided on both the dentist's and technician's specimens to eliminate the possibility of identification errors. This arrangement ensures that the patient's reference shade and hue are precisely known (1) at the time of patient examination by the dentist, (2) when the artificial tooth is fabricated, and (3) when the dental appliance is delivered to the dentist for installation in a patient.

OBJECTS AND SUMMARY OF THE INVENTION

Accordingly, it is an object of the present invention to provide an improved arrangement for matching artificial denture appliances with life-like shades and colors, or hues.

It is another object of the present invention to provide a shade and hue reference system for matching the shade and hue of an artificial denture with a desired life-like shade and hue in a foolproof arrangement which allows for verification of the artificial denture shade and hue prior to installation.

Yet another object of the present invention is to attach a patient's identifying information to a holder to which a first denture sample having a given hue and color is permanently attached, while allowing a second denture sample with matching hue and color and also having patient identifying data to be removed from the holder for transport to a denture manufacturer which permits verification of fabricated denture hue and color and eliminates the possibility of error or confusion in matching denture hue and color for a given patient.

A further object of the present invention is to provide a self-contained reference system for matching the shade of a dental appliance with a desired life-like color which can be re-used without limit.

A still further object of the present invention is to provide an improved dental tooth shade matching reference system which essentially eliminates the possibility of shade mismatches arising from mistake such as of the patient's specimen or identity and allows for precise matching of virtually any shade and hue.

Another object of the present invention is to provide a system to facilitate visual comparison of the shade/hue of a patient's natural teeth with the shade/hue of artificial teeth with which the patient is to be fitted.

Still another object of the present invention is to provide a safe, hygienic, disposable tab for insertion in a patient's mouth which affords a uniform color field for viewing artificial teeth adjacent to the patient's natural teeth for matching shade/hue of the artificial teeth with that of the natural teeth.

It is another object of the present invention to provide a generally flat panel having a neutral color and a plurality of artificial teeth arranged either by shade or hue for visually isolating the artificial teeth by displaying them on a uniform neutral color background which allows a viewer to concentrate on a particular shade or hue in matching a shade or hue of an artificial tooth with the shade or hue of a patient's natural teeth.

These objects of the present invention are achieved and the disadvantages of the prior art are eliminated by a dental tooth shade or hue matching reference guide for matching shade or hue of artificial teeth with the shade or hue of the patient's natural teeth or for providing artificial teeth with a life-like shade or hue, the reference guide comprising a panel with a solid, generally neutral color; and a plurality of reference teeth each having a different shade or hue, wherein the plurality of reference teeth are disposed adjacent to the panel such that the panel provides a uniform background color field when the reference teeth are viewed to facilitate distinguishing between different shades or hues.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

FIG. 13 is a sectional view of the reference master shade/hue guide shown in FIG. 12 taken along site line 13—13 therein;

DETAILED DESCRIPTION OF THE PREFERRED EMBODIMENTS

Figure 1:
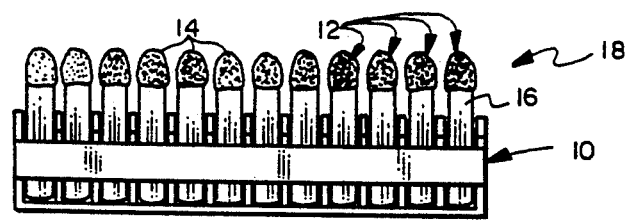
FIG. 1 is an elevation view of a prior art dental tooth shade guide.
Figure 2:
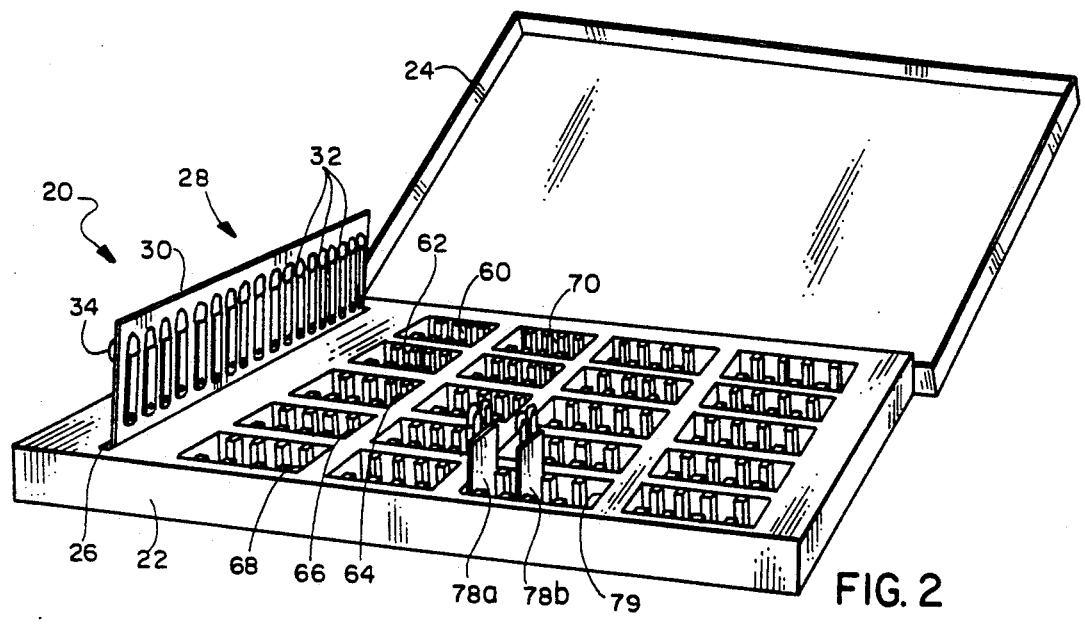
FIG. 2 is a perspective view of a dental tooth shade/hue matching reference system in accordance with the principles of the present invention.
Figure 3:
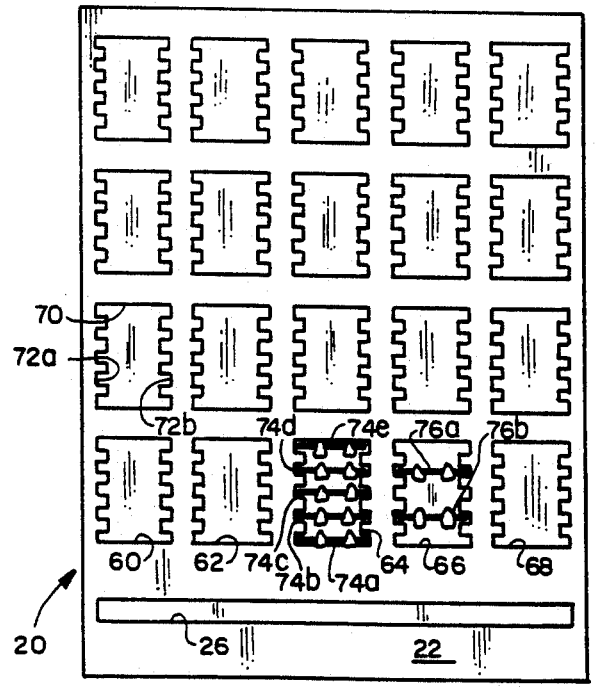
FIG. 3 is a plan view of the inventive dental tooth shade/hue matching reference system shown in FIG. 2.

Referring to FIG. 2, there is shown a perspective view of a dental tooth shade/hue matching reference system 20 in accordance with the principles of the present invention. A plan view of the shade/hue matching reference system 20 with cover removed is shown in FIG. 3. The shade/hue matching reference system 20 includes a generally rectangular base or carrier 22 having a removable or hinged cover 24. Base 22 includes a plurality of spaced, generally rectangular bins, or sample compartments, some of which are identified in FIGS. 2 and 3 as elements 60, 62, 64, 66, 68 and 70. Each of the bins includes a plurality of pairs of spaced recessed edge portions 72a, 72b as shown for bin 70 in FIG. 3. Each pair of aligned, recessed edge portions 72a, 72b for each of the bins in base 22 is adapted to receive and support a respective shade/hue unit. As shown in FIG. 3, bin 64 has positioned therein and provides support for five shade/hue units 74a-74e. Bin 66 is shown holding two such shade/hue units 76a and 76b. Each of the aforementioned shade/hue units is easily inserted in and removed from a respective bin by sliding it vertically. The bins provide support for and maintain the shade/hue units in a generally vertical orientation as shown for shade/hue units 78a and 78b in bin 79 in FIG. 2.

Base 22 further includes an elongated, generally linear shade/hue guide slot 26 adapted to receive and provide support for a reference master shade/hue guide 28. FIGS. 5a and 5b respectively show front and rear elevation views of the reference master shade/hue guide 28. The reference master shade/hue guide 28 includes a generally flat, elongated shade/hue guide panel 30 having on a first side a first set of shade/hue guide units 32 and on a second, opposed side a second set of shade/hue guide units 34. Each of the first and second shade/hue guide units 32, 34 includes a respective specimen tooth 32', 34' as also shown in the partial lateral sectional view of FIG. 4. Each of the shade/hue guide units 32, 34 further includes a respective support arm 36, 38 which is attached to an associated specimen tooth and provides support therefore. The specimen teeth 32' of the first set of shade/hue guide units 32 may be arranged in accordance with the shade of each of the specimen teeth. Similarly, the second set of shade/hue guide units 34 may be arranged on the second surface of the shade/hue guide panel 30 in accordance with the hue of the specimen teeth. The shades of the specimen teeth in the first and second sets are the same, but the sequence is different on each side of panel 30 creating an illusion that the shade guides are different.

As shown in FIGS. 5a and 5b, each of the support arms 36, 38 to which a respective specimen tooth 32', 34' is attached is also removably held by insertion into a receptacle such as designated 31 in FIG. 5b. The receptacles 31 are formed as recesses in the panel 30 with opposed inward projections 31a engaging and holding the support arm or tab 36 in a snap-fit.

In an alternate embodiment not illustrated, the support arms 36, 38 may be removably attached to the shade/hue guide panel 30 by means of an aperture in the bottom of the tab or arm and a mounting stud formed in the panel 30. A plurality of mounting studs are arranged in a spaced manner on opposing surfaces of the shade/hue guide panel 30 to allow for the first and second shade/hue guide units 32, 34 to be attached to or removed from the shade/hue guide panel. It will be observed, and it is considered an important feature of the inventive master shade guide, that the panel 30 extends above the sample teeth when they are received in their associated receptacles. This provides visual isolation by displaying the tooth on a uniform field (the panel may be blue, high density gray or white) and permits the user to concentrate his or her faculties on that particular shade or hue.

Ease in removal of each of the shade/hue guide units 32, 34 allows the shade/hue guide units to be replaced by a new one after an extended period of time of use to avoid discoloration of the specimen teeth 32', 34' which leads to inaccurate shade/hue matching with natural teeth. FIG. 5a shows the specimen teeth 34' arranged by shade from left to right in proceeding from light to dark shades. FIG. 5b shows the specimen teeth 32' arranged in groups by hue from left to right, with the specimen teeth varying in shade from light to dark in proceeding from left to right within each group. The facing surfaces of the shade/hue guide panel 30 are provided with a solid color for a viewing background for the specimen teeth, which color in a preferred embodiment is blue or neutral density gray.

Figure 4:
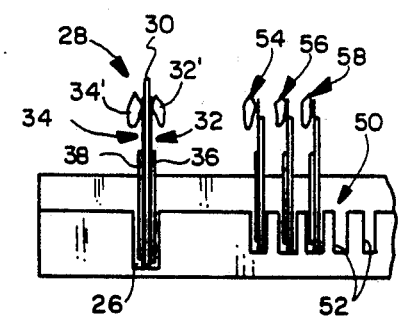
FIG. 4 is a partial lateral sectional view of the dental tooth shade/hue matching reference system shown in FIG. 3.
Figure 5A:
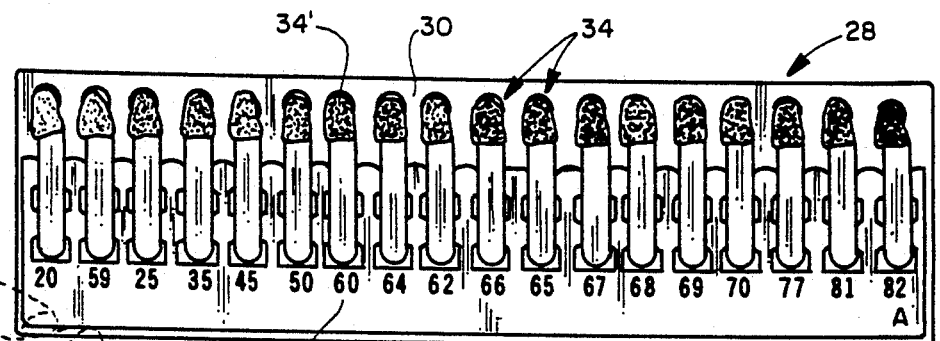
FIGS. 5a and 5b are respectively front and rear elevation views of a reference master shade/hue guide for use in the shade/hue matching reference system of the present invention.
Figure 5B:
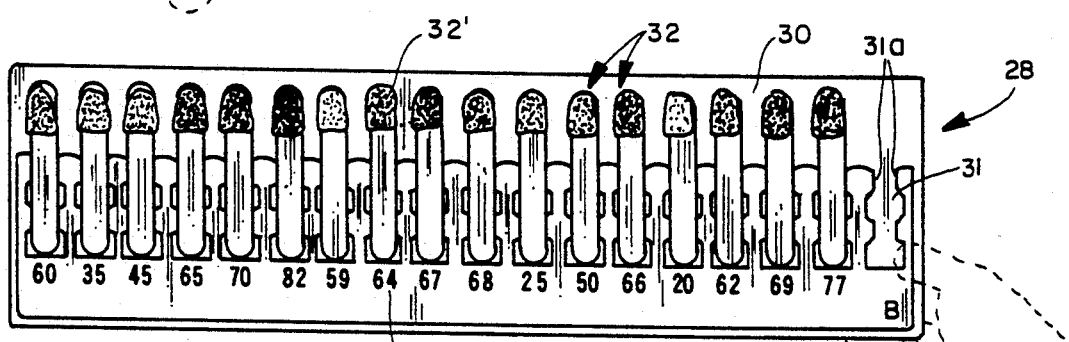

As shown in the partial sectional view of FIG. 4, bin 50 includes a plurality of spaced slots 52 each aligned with a pair of the aforementioned facing recessed edge portions within the bin for receiving a respective shade/hue unit, as shown for shade/hue units 54, 56 and 58 in the figure. As shown in the figures, when the shade/hue matching reference system 20 is in use, the reference master shade/hue guide 28 is maintained in a generally vertical orientation as are the various shade/hue units for ease of viewing by the dentist. When not in use, the reference master shade/hue guide 28 as well as the various shade/hue units may be removed from their respective support slots and either placed in a sample bin or laid flat on an upper surface of the base 22 to allow the cover 24 to be positioned on the base in a manner which protects and retains the reference master shade/hue guide as well as the various shade/hue units. In a preferred embodiment, two of the sample bins may be used to accommodate a plurality of shade/hue units adapted for providing dental appliances having custom-made dentures with one's individual shade and hue as described below.

Figure 6:
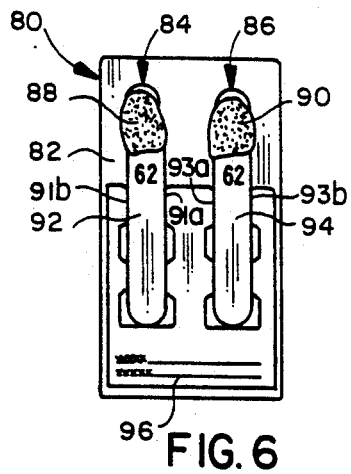
FIG. 6 is an elevation view of one embodiment of a tooth shade unit for use in the dental tooth shade/hue matching reference system of the present invention.

Referring to FIG. 6, there is shown an elevation view of a preferred embodiment of a shade/hue unit 80 for use in the present invention. Shade/hue unit 80 includes a holder, or base, 82 upon which a patient data record 96 may be entered. Attached to holder 82 are first and second shade/hue specimens 84 and 86. The holder 82 is also preferably a solid color, such as white, blue or neutral gray, forming a suitable background for viewing the first and second specimens 84, 86. Holder 82 extends above the first and second shade/hue specimens 84, 86 to highlight their shade and hue and facilitate focusing the viewer's attention on these specimens. The first shade/hue specimen 84 includes a first sample tooth 88 attached to a first end of a first handle 92. Similarly, the second shade/hue specimen 86 includes a second sample tooth 90 attached to a first end of a second handle 94. Each of the handles 92, 94 is inserted in a respective receptacle within holder 82 and is frictionally retained therein by means of a respective pair of spaced inward projections 91a, 91b and 93a, 93b. The first and second sample teeth 88, 90 are provided with the same shade and hue, with the appropriate shade/hue information disposed on the first and second handles 92, 94. Corresponding shade/hue data is also entered on the holder 82 as shown in the figure. One of the shade/hue specimens is permanently attached to holder 82, while the other shade/hue specimen is removable from the holder for shipment to the denture manufacturer or lab. Thus, in one embodiment, an epoxy cement 102, or other conventional adhesive material, may be used to fixedly attach first handle 92 to holder 82. Second handle 94 of the second shade/hue specimen 86 may be removed from the receptacle in holder 82. Once removed, the second specimen 86 may be shipped to a remote artificial tooth fabrication facility, with the shade and hue of the thus produced artificial tooth capable of accurate verification when received by the dentist prior to installation using the holder-mounted first shade/hue specimen 84.

Figure 7:
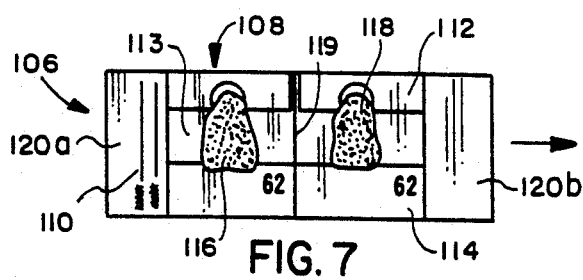
FIG. 7 is an elevation view of another embodiment of a tooth shade/hue unit for use in the dental tooth shade/hue matching reference system of the present invention.

Referring to FIG. 7, there is shown an elevation view of another embodiment of a tooth shade/hue unit 106 for use in the dental tooth shade/hue matching reference system of the present invention. Shade/hue unit 106 includes a holder 108 comprised of an upper brace 112, a lower brace 114, and first and second end braces 120a, 120b connecting the upper and lower braces. A center brace 119 also connects the upper and lower braces 112, 114. The upper and lower braces 112, 114 are disposed forward of the first and second end braces 120a, 120b, with an inter-brace space 113 disposed intermediate the upper and lower braces. First and second sample teeth 116 and 118 are adapted for sliding insertion within the inter-brace space 113 between the upper and lower braces 112, 114. A tab on the rear of each of the first and second sample teeth 116, 118 allows the sample teeth to be inserted in the inter-brace space 113 and maintained therein by engagement of the tab by the upper and lower braces 112, 114. The rear tabs on each of the first and second sample teeth 116, 118 are not shown in the figure for simplicity. The first end brace 120a is adapted to receive patient indicia and further includes shade/hue information. Similarly, adjacent spaces on the lower brace 114 adjacent the first and second sample teeth 116, 118 include shade/hue data characteristic of the shade and hue of the first and second sample teeth 116, 118. As in the previously discussed shade/hue unit, the shade and hue of each of the first and second sample teeth 116, 118 are identical. The first sample tooth 116 may be permanently mounted in the holder 108 by conventional means such as by an epoxy cement, while the second sample tooth 118 may be removed from the holder 108 in the direction of the arrow and shipped to a manufacturer of artificial teeth. Upon its return, the shade and hue of the manufactured denture may be compared with that of the first sample tooth 116 for verifying the shade and hue of the artificial tooth in accordance with the present invention.

Figure 8A:
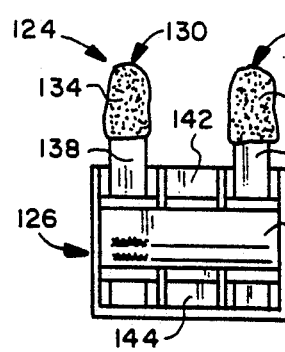
FIGS. 8a and 8b are respectively front and rear elevation views of yet another embodiment of a tooth shade/hue unit for use in the present invention.
Figure 8B:
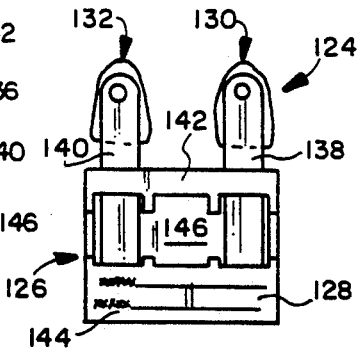

Referring to FIGS. 8a and 8b, there are respectively shown front and rear elevation views of yet another shade/hue unit 124 for use in the dental tooth shade/hue matching reference system of the present invention. Shade/hue unit 124 includes a holder 126 comprised of an upper brace 142, a lower brace 144, and an intermediate brace 146. Disposed on the intermediate brace 146 is sample tooth shade/hue information as well as a space to enter patient indicia. Similarly, disposed on an opposed surface of the lower brace 144 is a location for the entry of patient indicia 128. Inserted in holder 126 are first and second shade/hue specimens 130 and 132. The first shade/hue specimen 130 includes a first sample tooth 134 attached to one end of a first support arm or tab 138. Similarly, the second shade/hue specimen 132 includes a second sample tooth 136 attached to a first end of a second tab 140. Respective second ends of the first and second tabs 138, 140 are adapted to engage a lower portion of the holder 126. The second, or lower, end of the first tab 138 is fixedly attached to the holder 126 by conventional means such as an epoxy cement, which is not shown for simplicity. Other conventional means may be employed for permanently attaching the first tab 138 to holder 126. The lower end of the second tab 140 is provided with a locking tab for engaging a lower portion of the holder 126 in a removable manner which permits insertion into and retraction from the holder 126 of the second shade/hue specimen 132. Other conventional means well known to those skilled in the relevant arts may be employed for removably attaching the second tab 140 to holder 126, although these are not shown for simplicity. Each of the first and second tabs 138, 140 includes on the surface thereof, shade/hue information relating to the shade and hue of the two sample teeth 134, 136 which are identical for both teeth. In this manner, the second sample tooth 136 may be removed from the holder 126 and shipped to an artificial tooth manufacturer having the correct shade/hue information imprinted thereon, while the dentist treating the patient retains the holder 126 and the first sample tooth 134 having patient indicia as well as relevant shade/hue information. This permits verification of the shade and hue of the thus manufactured appliance when received by the dentist.

Figures 9A, 9B:
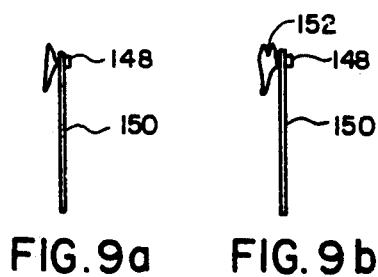
FIGS. 9a and 9b are elevation views of a tooth specimen and supporting handle for use in fabricating an artificial tooth having a custom-made shade and hue respectively showing the specimen tab before and after applying the artificial tooth material.

Referring to FIGS. 9a and 9b, there are shown elevation views of a tab 148 and a supporting handle 150 for use in fabricating an artificial tooth having a custom-made shade and hue respectively showing the specimen tab before and after applying the artificial tooth material. Tab 148 is used as a base, or foundation, for building up the tooth specimen 152. The tooth specimen is matched in hue and color with the patient's real teeth, or to provide a life-like shade and hue. The tooth specimen 152 is also shaped as desired and may be formed from composite materials or a cold cure colored powder. Tab 148 is attached to the support handle 150 to facilitate forming the artificial tooth specimen 152 and for subsequent transport to a denture manufacturer or lab.

Figure 10:
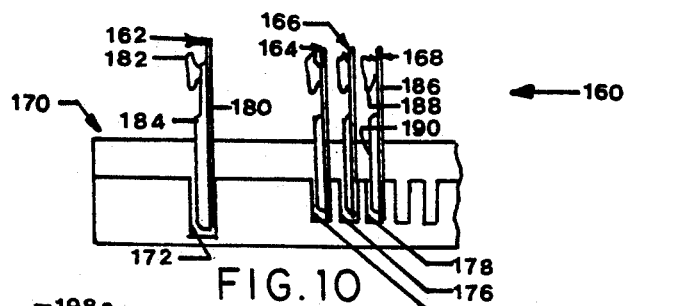
FIG. 10 is a partial lateral sectional view of another embodiment of a dental tooth shade/hue matching reference system in accordance with the present invention which employs a single-sided background viewing panel for use in a reference master shade/hue guide as well as in a plurality of shade/hue units.

Referring to FIG. 10, there is shown a partial lateral sectional view of another embodiment of a dental tooth shade/hue matching reference system 160 in accordance with the principles of the present invention. The shade/hue matching reference system 160 includes a reference master shade/hue guide 162 in combination with a plurality of shade/hue units such as first, second and third shade/hue units 164, 166 and 168. Each of the shade/hue units 164, 166 and 168 includes a pair of support arms 186 to which is attached a respective specimen tooth 188 as well as background shield 186 as described below. Each shade/hue unit 164, 166 and 168 is inserted in and supported in a generally upright orientation by a respective slot 174, 176 and 178 in base 170. The reference master shade/hue guide 162 includes a plurality of reference specimen teeth 182 each attached to a respective support arm 184, although only a single specimen tooth and support arm are shown in the sectional view of FIG. 10 for simplicity. Each of the support arms 184 is removably attached to a single side of a generally planar, panel-like background shield 180 in accordance with the present invention. Background shield 180 in combination with the plurality support arms 184 attached thereto is adapted for insertion into an elongated, longitudinal shade/hue guide support slot 172 within a base 170. Support slot 172 securely maintains the reference master shade/hue guide 162 in a generally upright orientation as shown in FIG. 10 for storage, transport or display. Background shield 180 is typically comprised of a plastic material and has a uniform neutral color such as white, neutral blue or neutral gray which provides a specimen tooth viewing background enabling the viewer to focus on the shades and hues of the specimen teeth without being distracted by surrounding colors.

Figure 11:
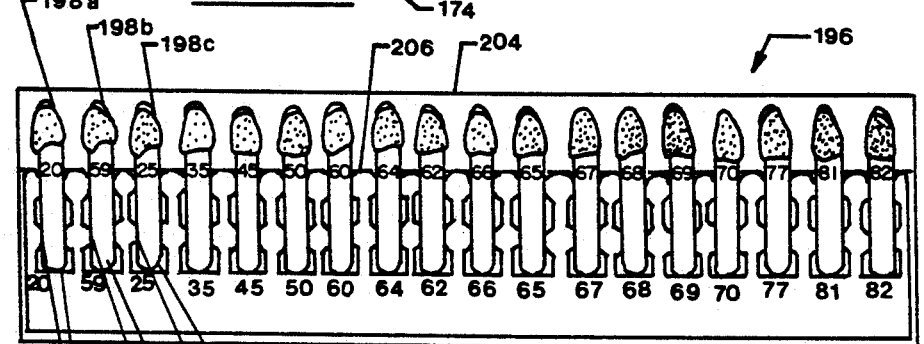
FIG. 11 is a front elevation view of a reference master shade guide incorporating a background shield aft of the sample teeth which facilitates viewing of the sample teeth in accordance with one aspect of the present invention.

Referring to FIG. 11, there is shown an elevation view of a reference master shade guide 196 for use in the present invention. The reference master shade guide 196 includes a plurality of spaced specimen teeth aligned in a generally linear array from light shade to dark shade in proceeding from left to right in the figure. The three specimen teeth labeled 198a, 198b and 198c are the three lightest specimen teeth in the reference master shade guide 196.

The reference master shade guide 196 includes an upper background shield 204 extending upward from an upraised support portion 206. The upraised support portion 206 includes a plurality of spaced retaining slots, with the three left-most retaining slots identified as elements 202a, 202b and 202c. The retaining slots are arranged in a spaced linear array along the length of the upraised support portion 206 and are adapted to receive and provide support for a respective support arm attached to a specimen tooth. Thus, retaining slots 202a, 202b and 202c within the upraised support portion 206 receive and engage support arms 200a, 200b and 200c respectively attached to reference master shade specimen teeth 198a, 198b and 198bc. Each of the support arms may be manually removed from its associated retaining slot and includes shade identifying data corresponding to the shade identifying data disposed immediately below its associated specimen tooth on the reference master sheet guide 196 as shown in FIG. 11. It should be noted that the background shield 204 extends above all of the specimen teeth to provide a uniform background color field for viewing these specimen teeth free of distraction from surrounding colors.

Figure 12:
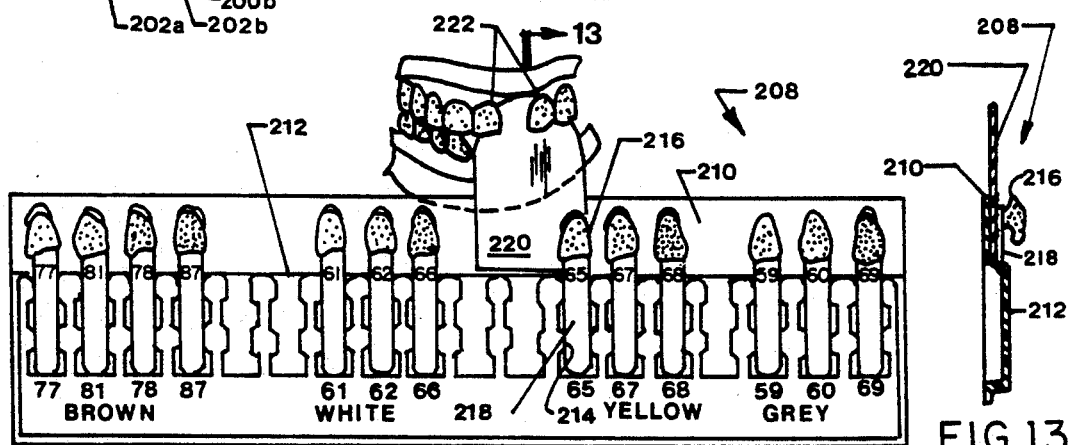
FIG. 12 is a front elevation view of a reference master hue guide incorporating a sample teeth background viewing shield as well as a background viewing tab for insertion in a patient's mouth to facilitate comparison of sample teeth shade/hue with that of the patient's natural teeth.

Referring to FIG. 12, there is shown a front elevation view of a reference master hue guide for use in the shade/hue matching reference system of the present invention. The reference master hue guide 208 includes a plurality of specimen teeth and support arm combinations arranged in a linear, spaced array on a specimen support portion 212. The specimen support portion 212 includes a plurality of spaced retaining slots 214 each adapted to receive and retain in tight fitting engagement a respective support arm 218 to which is attached a specimen tooth 216. As shown in the figure, the specimen teeth are arranged in four groups by hue, with the four hue groups being brown, white, yellow and grey. Within each hue group, the specimen teeth are arranged by shade, such as from light to dark in proceeding from left to right within each hue group. Extending above and integral with the specimen support portion 212 is a background shield 210 disposed aft of and extending above each of the specimen teeth. As in the case the reference master shade guide 196 described above, the background shield 210 in the reference master hue guide 208 is preferably a neutral color, such as white, neutral blue or neutral gray, for providing a uniform background color field when viewing the specimen teeth without the distraction of surrounding colors. The reference master shade guide 196 shown in FIG. 11 and the reference master hue guide 208 shown in FIG. 12 are each disposed on a single side of the background shield.

Also shown in FIG. 12 with the reference master view guide 208 is a background tab 220 adapted for insertion intermediate the background shield 210 and the various specimen teeth. Background tab 220 is further adapted for insertion in the mouth of a patient as shown in the figure for positioning aft of the patient's teeth 222. As in the case of background shield 210, the background tab 220 is preferably a neutral color such as white, neutral blue or neutral gray for providing a uniform color field when viewing and comparing the specimen teeth with the patient's natural teeth 222.

Referring to FIG. 12 as well as to FIG. 13, which is a sectional view taken along site line 13—13 in FIG. 12, additional details of the combination of the reference master hue guide 208 and the background tab 220 will now be described. Background tab 220 is preferably comprised of a semi-rigid styrene plastic and includes a straight lower edge and a curved upper edge to facilitate insertion of the background tab in the mouth of a patient. The upper curved edge of the background tab 220 is preferably deburred to prevent cutting the tissue in the area of the patient's mouth. The lower, straight edge of the background tab 220 is adapted for positioning in contact with an upper edge of the specimen support portion 212 of the reference master hue guide 208 when the background tab is inserted intermediate the background shield 210 and one or more specimen teeth. Each of the specimen teeth 216 is attached to and supported by a respective support arm 218 which is inserted in a respective slot 214 as in the previously described embodiment. The background tab 220 is used as an extension of the background shield 210 to improve viewing of the specimen teeth 216 as well as the patient's natural teeth 222. The background tab 220 is disposable and thus saves the user, i.e., the administering dentist or dental technician, the time required to sterilize the entire shade/hue guide after prior use by another patient. Use of background tab 220 avoids contact of the reference master hue guide 208 with the patient's mouth in dramatically reducing the possibility of transmission of communicable diseases and eliminates the requirement to sterilize the reference master hue guide after each use. The background tab 220 is adapted for tight fitting insertion between and engagement with the background shield 210 and a support arm 218 to which a specimen tooth 216 is attached. The lower, straight edge of the background tab 220 engages and is supported by an upper edge of the specimen support portion 212 of the reference master hue guide 208.

Figure 14:
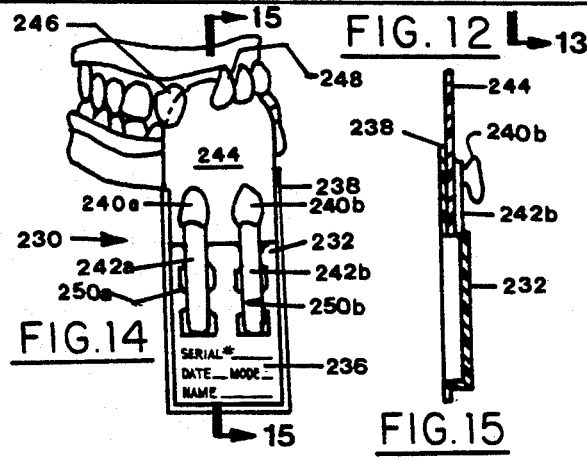
FIG. 14 is a an elevation view of a tooth shade/hue unit incorporating a background viewing tab inserted in the mouth of a patient to facilitate comparison of sample teeth shade/hue with the shade/hue of the patient's natural teeth.
Figure 16:
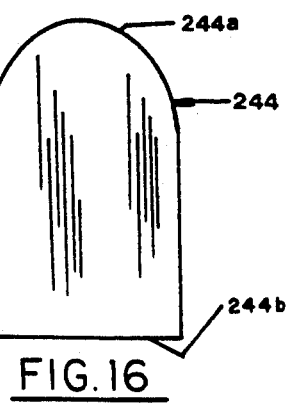
FIG. 16 is an elevation view of a background viewing tab which facilitates comparison of the shade/hue of sample teeth with the shade/hue of one's natural teeth in accordance with another aspect of the present invention.

Referring to FIG. 14, there is shown an elevation view of a shade/hue unit 230 in combination with a background tab 244 in accordance with another aspect of the present invention. An elevation view of background tab 244 is shown in FIG. 16. The shade/hue unit 230, as in the case of the shade/hue unit 80 shown in FIG. 6 and described above, includes first and second specimen teeth 240a and 240b having the same shade and hue. Shade/hue unit 230 is intended for use with a plurality of similar shade/hue units wherein the specimen teeth have a different shade and/or hue in the various units. Each of the first and second specimen teeth 240a, 240b is attached to an upper portion of a respective support arm 242a and 242b. Each of the support arms 242a, 242b is, in turn, inserted in and supported by a respective slot 250a and 250b in the specimen support portion 232 of the shade/hue unit 230.

Figure 15:
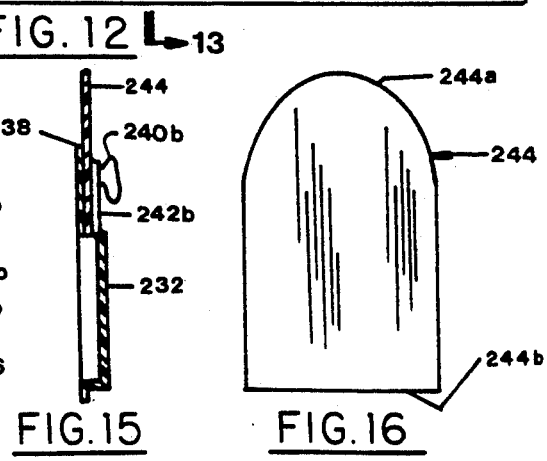
FIG. 15 is a sectional view of the tooth shade/hue unit together with background viewing tab shown in FIG. 14 taken along site line 15—15 therein.

As shown in the sectional view of FIG. 15 taken along site line 15—15 in FIG. 14, background tab 244 is inserted intermediate and in tight fitting engagement with a background shield 238 of the shade/hue unit 230 and the support arms to which the specimen teeth are attached. The lower flat edge of the background tab rests upon and is supported by an upper edge of the specimen support portion 232 of the shade/hue unit 230. The upper curved edge of the background tab 244 is inserted in the mouth of a patient behind his or her teeth 246 and 248 to facilitate comparison of the shade and hue of the specimen teeth 240a, and 240b with that of the patient's natural teeth. Disposed on the specimen support portion 232 is a patient data record 236 for identifying the patient for which the shade/hue specimen is selected for fabrication of an artificial tooth. As in the previously described embodiments, at least one of the first and second specimen teeth 240a, 240b is removable from the shade/hue unit 230 for transport to a denture manufacturer or lab. Each of the support arms 242a, 242b contains the same shade/hue identifying data which is recorded on the patient data record 236 prior to sending one of the specimen teeth to the aforementioned denture manufacturer or lab.

As shown in the elevation view of FIG. 16, background tab 244 includes a lower straight edge 244b and an upper curved edge 244a which is deburred to a very smooth edge surface for safe insertion in a patient's mouth. The background tab 244 is preferably comprised of a semi-rigid, styrene plastic and is of a neutral, single color for providing a uniform color background field and is intended to be disposable.

There has thus been shown a system for providing artificial teeth with life-like shade and hue, or for matching the shade and hue of an artificial tooth with the shade and hue one's natural teeth, which system employs a single-sided master shade/hue guide and/or a plurality of single-sided paired sample teeth, with each pair attached to a holder and having a given shade and hue corresponding to a tooth in the master shade/hue guide. The single-sided master shade/hue guide as well as all of the single-sided paired sample teeth are adapted to receive a background shield for insertion in a patient's mouth to permit the juxtaposed comparison of the sample teeth with the patient's natural teeth. The low cost, disposable background tab provides an extended uniform color field for permitting sample teeth in either the master shade/hue guide or a shade/hue unit to be closely compared with a shade/hue of the patient's natural teeth for improved artificial tooth shade/hue matching. The neutral color of the background panel, such as white, neutral blue or neutral gray, allows the viewer to focus on the shades and hues of the specimen and natural teeth and not be distracted by surrounding colors. The single-sided master shade/hue guide and each of the plurality of single-sided paired sample teeth units include a background shield positioned behind and extending above the specimen teeth to provide an extended uniform background color field for simultaneous viewing of the specimen teeth and the patient's natural teeth.

While particular embodiments of the present invention have been shown and described, it will be obvious to those skilled in the art that changes and modifications may be made without departing from the invention in its broader aspects. For example, the shade/hue matching reference system may be used for only matching artificial tooth shade or for only matching artificial tooth hue. Similarly, the system may be used with the combination of a shade/hue reference master guide in combination with a plurality of shade/hue specimen teeth units each having a different shade and hue, or may be used only with the shade/hue reference master guide or only with the plurality of different shade/hue specimen teeth units in matching the shade/hue of artificial teeth with the shade/hue of a patient's natural teeth or for providing artificial teeth with a lifelike shade and hue. In addition, while some of the specimen teeth are disclosed as attached to a holder by means of a mounting stud inserted through an aperture in a handle, various other mounting arrangements well known to those skilled in the relevant arts could as easily be employed. For example, the handle may be sized to engage tabs on the holder in a tight-fitting manner to allow for frictional retention of the handle and the specimen tooth attached thereto. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

I claim:

1. A dental tooth shade/hue matching reference system for matching the shade/hue of artificial teeth with the shade/hue of a patient's natural teeth or for providing artificial teeth with a like-like shade/hue, said system comprising:

a plurality of shade/hue units having a shade/hue of a patient's natural teeth or having a life-like shade/hue, wherein each shade/hue unit includes:

a holder having shade/hue identifying date and a patient identification area; and first and second shade/hue specimen teeth each having the same shade/hue, wherein the shade and hue of said specimen teeth of each shade/hue unit vary over a range of shades and hues and wherein at least one of said shade/hue specimen teeth is removably attached to said holder, and wherein said holder further includes a background panel disposed adjacent and aft of said specimen teeth for providing a uniform background color field when viewing said specimen teeth and eliminating distracting surrounding colors.

2. The dental tooth shade/hue matching reference system of claim 1 wherein said background panel is white, neutral blue or neutral gray in color.

3. The system of claim 2 wherein each holder comprises a generally flat background panel adapted to receive and support a respective pair of first and second shade/hue specimen teeth.

4. The system of claim 3 wherein each holder includes mounting means for removably coupling at least one of said shade/hue specimen teeth to said holder.

5. The system of claim 4 wherein each of said mounting means couples at least one of said shade/hue specimen teeth to said holder in a sliding manner.

6. The system of claim 4 further comprising first and second support arms for respectively coupling a pair of said first and second shade/hue specimen teeth to a respective holder.

7. The system of claim 6 wherein each holder includes permanent affixing means for attaching said first support arm to a respective holder.

8. The system of claim 6 wherein each holder further includes snap-acting coupling means for removably attaching said second support arm to said holder.

9. The system of claim 1 further comprising a shade/hue reference guide having a plurality of reference teeth each having a different shade/hue.

10. A dental tooth shade/hue matching reference system for matching the shade/hue of artificial teeth with the shade/hue of a patient's natural teeth or for providing artificial teeth with a life-like shade/hue, said system comprising:

a shade/hue unit having a shade/hue of a patient's natural teeth or having a life-life shade/hue, wherein said shade/hue unit includes:

a holder;

first and second shade/hue specimen teeth each having the same shade/hue, wherein at least one of said shade/hue specimen teeth includes a support arm sized to be easily handled by a thumb and forefinger grip of a user and removably attached to said holder, and characterized in that said holder includes shade/hue identifying data for said specimen teeth and a patient identification area, and said support arm of said removable specimen tooth includes shade/hue identifying data; and a background tab of a generally neutral, solid color adapted for attachment to said holder and positioning aft of said specimen teeth, wherein said background tab is further adapted for positioning in or adjacent to a patient's mouth to facilitate juxtaposed comparison of the shade/hue of said specimen teeth with that of the patient's natural teeth by providing a uniform background color field for viewing said specimen teeth and the patient's natural teeth.

11. The dental tooth shade/hue matching reference system of claim 10 wherein said background tab is thin and generally flat and white, neutral blue or neutral gray in color.

12. The dental tooth shade/hue matching reference system of claim 11 wherein said background tab is comprised of a semirigid plastic.

13. The dental tooth shade/hue matching reference system of claim 12 wherein said plastic is styrene.

14. The dental tooth shade/hue matching reference system of claim 10 wherein said background tab includes a first generally flat, straight edge adapted for engaging said holder and a second curved edge adapted for positioning in or adjacent to a patient's mouth.

15. The dental tooth shade/hue matching reference system of claim 14 wherein said second curved edge is deburred.

16. The dental tooth shade/hue matching reference system of claim 10 wherein said background tab is disposable.

17. A dental tooth shade/hue matching reference system for matching the shade/hue of artificial teeth with the shade/hue of a patient's natural teeth or for providing artificial teeth with a life-like shade/hue, said system comprising:

a shade/hue reference guide having a plurality of reference teeth each having a different shade/hue;

a plurality of shade/hue units each having a shade/hue corresponding to the shade/hue of one of the reference teeth, wherein each shade/hue unit includes:

a holder; and first and second shade/hue specimen teeth each having the same shade/hue as one of the reference teeth, wherein at least one of said shade/hue specimen teeth is removably attached to said holder, and wherein said holder includes shade/hue identifying data and a patient identification area; and a background tab of generally neutral solid color adapted for attachment to either said holder or to said reference guide for positioning aft of said reference teeth, wherein said background tab is further adapted for positioning in or adjacent to a patient's mouth to facilitate juxtaposed comparison of the shade/hue or said reference teeth with that of the patient's natural teeth by providing a uniform background color field for viewing said reference teeth and the patient's natural teeth.

18. The dental tooth shade/hue matching reference system of claim 17 wherein said background tab is thin and generally flat and white, neutral blue or neutral gray in color.

19. The dental tooth shade/hue matching reference system of claim 18 wherein said background tab is comprised of a semi-rigid plastic.

20. The dental tooth shade/hue matching reference system of claim 19 wherein said plastic is styrene.

21. The dental tooth shade/hue matching reference system of claim 17 wherein said background tab includes a first generally flat, straight edge adapted for engaging said holder and a second curved edge adapted for positioning in or adjacent to a patient's mouth.

22. The dental tooth shade/hue matching reference system of claim 21 wherein said second curved edge is deburred.

23. The dental tooth shade/hue matching reference system of claim 17 wherein said background tab is disposable.

* * * * *